United States Patent [19]

Dittrich et al.

[11] Patent Number: 5,110,969
[45] Date of Patent: May 5, 1992

[54] METHOD OF MANUFACTURING OF OLIGO(4-(2-ORGANO-ORGANOOX-YSILYLALKYL)CYCLOHEXANE-1,2-DIYL)-BIS-OLIGOSULFIDES

[75] Inventors: Uwe Dittrich; Sigrid Dathe, both of Dresden; Hartmut Raabe; Rolf Sourisseau, both of Gotha; Klaus Ruehlmann, Dresden, all of Fed. Rep. of Germany

[73] Assignee: Chemiewerk Nuenchritz GmbH, Nuenchritz, Fed. Rep. of Germany

[21] Appl. No.: 729,544

[22] Filed: Jul. 15, 1991

[30] Foreign Application Priority Data

Jul. 13, 1990 [DE] Fed. Rep. of Germany ......... 342751

[51] Int. Cl.$^5$ ............................. C07F 7/08; C07F 7/18
[52] U.S. Cl. ....................................... 556/427
[58] Field of Search ........................................ 556/427

[56] References Cited

U.S. PATENT DOCUMENTS

| | | | |
|---|---|---|---|
| 4,384,132 | 5/1983 | Schwarz et al. | 556/427 |
| 4,408,064 | 10/1983 | Schwarz et al. | 556/427 X |
| 4,725,630 | 2/1988 | Magee et al. | 556/427 X |

Primary Examiner—Arthur C. Prescott
Attorney, Agent, or Firm—Oblon, Spivak, McClelland, Maier & Neustadt

[57] ABSTRACT

The invention relates to a method of manufacturing oligo(4-(2-organo-organooxysilylalkyl)cyclohexane-1,2-diyl)bis-oligosulfides from products of industrial-scale synthesis of 4-(2-organo-organooxysilylalkyl)-1-cyclohexene, without the use of catalysts and at normal pressure. The products produced are used as silane binders and adhesives, and as strengthening additives in silicate filled rubber mixtures. According to the invention, an organosilane of general formula

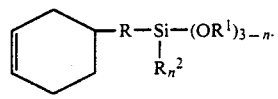

I containing an organochlorosilane of general formula

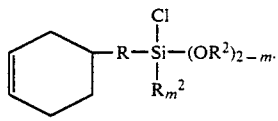

II where R and $R^2$ each independently represent an $C_{1-6}$ alkyl group;
$R^1$ represents an alkyl, cycloalkyl, or aryl group;
n = 1 to 3; and
m = 1 or 2; with the molar ratio of I to II being in the range 1000:1 to 10:1, is reacted directly with sulfur, in a molar ratio of R:sulfur (and/or hydrogen sulfide) of 1:1 to 1:5, at temperatures >150° C.

6 Claims, 2 Drawing Sheets

METHOD OF MANUFACTURING OF OLIGO(4-(2-ORGANO-ORGANOOXYSILYLALK-YL)CYCLOHEXANE-1,2-DIYL)BIS-OLIGOSULFIDES

BACKGROUND OF THE INVENTION

1. Field of the Invention

The invention relates to a novel and simple method of manufacturing oligo(4-(2-organoorganooxysilylalkyl)-cyclohexane-1,2-diyl)bis-oligosulfides.

2. Discussion of the Background

Sulfur containing organosilanes are used as silane adhesives or strengthening additives in silicate filled rubber mixtures, for applications such as, among others, vehicle tire treads and bodies. Sulfur-containing silane adhesives can also be used in manufacturing sealing compositions, molds for metal casting, colored and protective coatings, adhesives, asphalt mixtures, and silicate filled plastics. There are also possible applications in the area of fixing functional groups and substances to inorganic substrates, in, e.g., immobilizing of enzymes, manufacturing of fixed bed catalysts, and liquid chromatography.

Various methods may be used to produce sulfur-containing organosilicon compounds. Thus, it is known to produce bis(organo-organooxysilyl)oligosulfides, preferably bis(alkylorganooxysilyl)oligosulfides or mercaptoalkylalkoxysilanes, by reacting haloalkyltrialkoxysilanes (particularly halopropyltrialkoxysilanes) with $Met_2S_x$ and/or MetSH (where Met represents $NH_4$, Na, or K, and x=1 to 6) (DE-2,141,159 and DE-2,212,239; and U.S. Pat. Nos. 3,978,103 and 4,048,206). In this connection, the polysulfide $Met_2S_x$ can also be prepared in situ from MetOR (where R represents alkyl or cycloalkyl), MetSH, and S (DE-2,542,534, DE-2,712,966, and DE-3,311,340).

Further, the preparation of bis[(β-trialkoxysilylethyl)benzyl]oligosulfides by reacting β-trialkoxysilylethylbenzyl halides with NaHS and S is known (DE-3,504,241). The reaction of haloalkylalkoxysilanes with S and $H_2S$ in the presence of an amine or $NH_3$ to form alkoxysilylalkyl polysulfides has also been described (DE-2,648,241).

Further, mercaptoalkylalkoxysilanes, preferably mercaptopropylalkoxysilanes, can be converted to bis(organoorganooxysilyl)oligosulfides, preferably bis(propylorganooxysilyl)oligosulfides. According to DE-2,141,160, $S_zHal_2$ can be used for this (where z=1 to 3, and Hal represents Cl or Br; or according to DE-2,405,758, sulfur can be used.

In these methods it is a disadvantage that one must use special sulfidization agents, e.g. polysulfides or hydrogen sulfide or sulfur halides. In addition, there are undesired reaction products such as metal halides or hydrogen halides, which must be separated out in an additional process step. The use of mercaptosilanes necessitates an additional preliminary process step which is quite costly.

In the reaction of vinylsilanes with S and/or with a mixture of S and $H_2S$ according to DE-2,056,229, the abovementioned disadvantages are avoided. However, the reaction, which is carried out at 100°-200° C., leads to the desired products only when carried out at elevated pressure and in the presence of a sulfidization catalyst. Further, the free mercapto groups, which are unavoidably produced in a side reaction, substantially reduce the times for pre-vulcanization and vulcanization to completion, as is well known. The consequences of this, in addition to reduced production safety, are inadequate intermixing of the components of the vulcanizate and, ultimately, a rubber with inferior physical and mechanical parameters.

SUMMARY OF THE INVENTION

Accordingly, one object of the present invention is to devise a method of manufacturing oligo(4-(2-organoorganooxysilylalkyl)cyclohexane-1,2-diyl)bis-oligosulfides from the products of synthesis of 4-(2-organoorganooxysilylalkyl)-1-cyclohexene, which method is easy to accomplish on an industrial scale and which does not require elevated pressure or the use of special sulfidization catalysts. Another object of the invention is to begin with the products of synthesis of 4-(2-organo-organooxysilylalkyl)-1-cyclohexene such that the SiCl-containing components contained therein do not have an adverse effect on the reaction. The compounds produced should be usable as silane binders or adhesives or as strengthening agents in silicate filled rubber mixtures.

The object of the present invention is provided for by reacting an organosilane of general formula

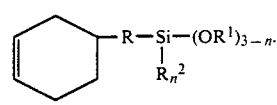

I and an organochlorosilane of general formula

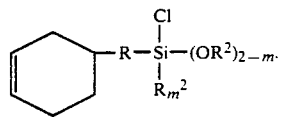

II wherein R and $R^2$ each independently represent a $C_{1-6}$ alkyl group;
$R^1$ represents an alkyl, cycloalkyl, or aryl group;
n=1 to 3; and
m=1 or 2;
wherein the molar ratio of I to II is in the range of from 1000:1 to 10:1, directly with sulfur or a mixture of hydrogen sulfide and sulfur, in a molar ratio of R: sulfur (and/or hydrogen sulfide) of 1:1 to 1:5, at a temperature > 150° C.

BRIEF DESCRIPTION OF THE DRAWINGS

A more complete appreciation of the invention and many of the attendant advantages thereof will be readily obtained as the same becomes better understood by reference to the following detailed descriptive when considered in connection with the accompanying drawings, wherein.

DETAILED DESCRIPTION OF THE PREFERRED EMBODIMENTS

Figure 1:
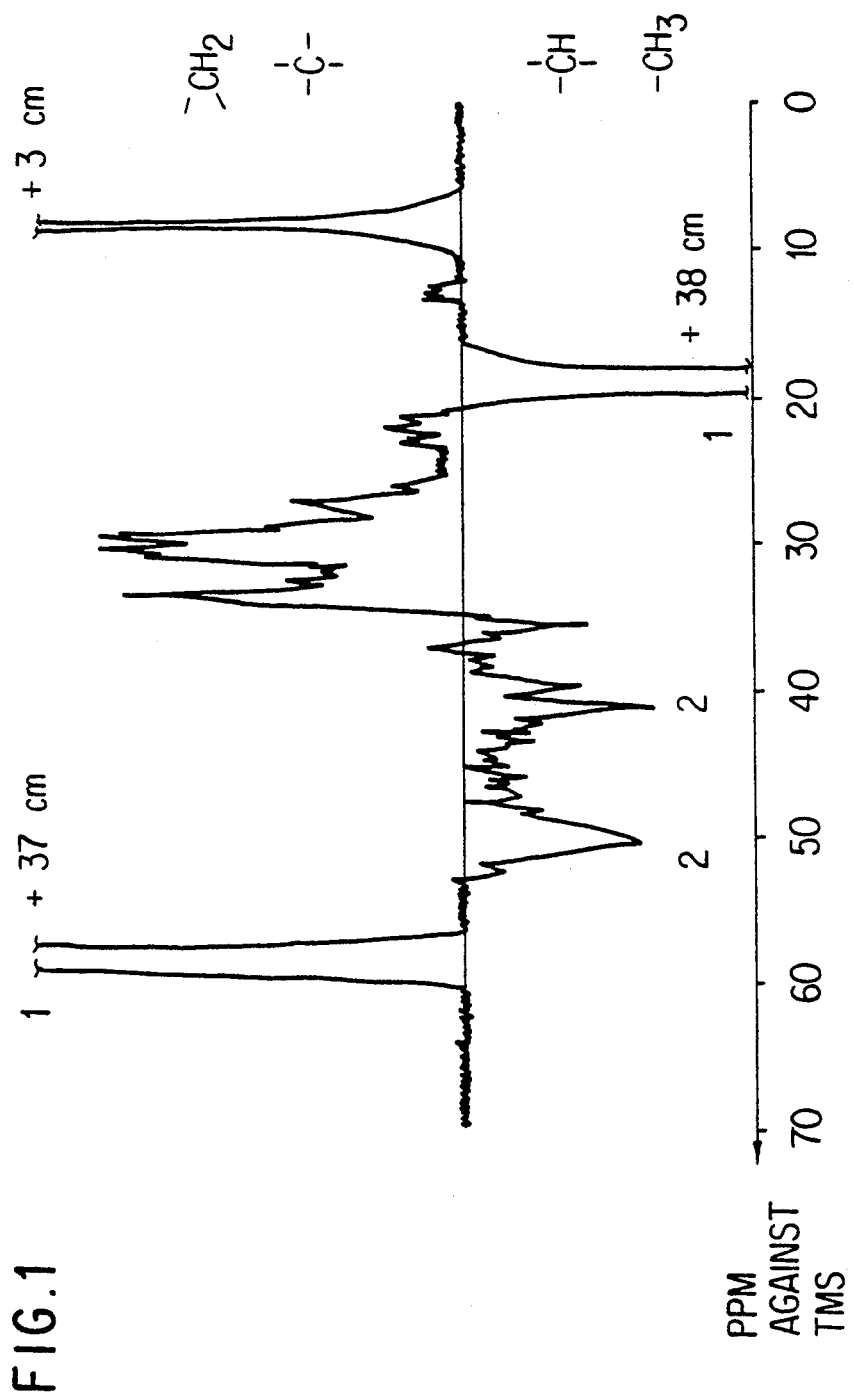
FIG. 1 sets out a $^{13}$C-NMR spectrum (Attached Proton Test) of the inventive S-containing silanes according to Example 1.

According to the invention, these objects are achieved by reacting an organosilane of general formula $$\text{[cyclohexene]}-R-\underset{\underset{R_n^2}{|}}{Si}-(OR^1)_{3-n}. \quad \text{I}$$

and an organochlorosilane of general formula $$\text{[cyclohexene]}-R-\underset{\underset{R_m^2}{|}}{\overset{\overset{Cl}{|}}{Si}}-(OR^2)_{2-m}. \quad \text{II}$$

wherein R and $R^2$ each independently represent a $C_{1-6}$ alkyl group;
$R^1$ represents an alkyl, cycloalkyl, or aryl group;
$n = 1$ to 3; and
$m = 1$ or 2;
   wherein the molar ratio of I to II is in the range of from 1000:1 to 10:1,
directly with sulfur or a mixture of hydrogen sulfide and sulfur, in a molar ratio of R: sulfur (and/or hydrogen sulfide) of 1:1 to 1:5, at a temperature $> 150°$ C., preferably at a temperature between 150° and 200° C. Preferably the molar ratio of I to II is in the range of from 1000:1 to 100:1. When a mixture of sulfur and hydrogen sulfide is employed, the weight fraction of the sulfur is preferably between 0.01 and 0.1 kg/kg, based on the amount of silane employed. The method of the present invention is conducted at an ambient reaction pressure, preferably from 0.8–1.2 atmospheres, more preferably from 0.95–1.05 atmospheres.

The inventively produced oligo(4-(2-organoorganooxysilylalkyl)-cyclohexane-1,2-diyl)-bis-oligosulfides have general formula $$\left[\begin{array}{c} -S_{\frac{x}{2}}- \\ -S_{\frac{x}{2}}- \end{array}\text{[cyclohexane]}-R-\underset{\underset{R_n^2}{|}}{Si}-(OR^1)_{3-n}\right]_m \quad \text{III}$$

where R and $R^2$ each independently represent a $C_{1-6}$ alkyl group;
$R^1$ represents an alkyl, cycloalkyl, or aryl group;
$n = 1$ to 3; and
$m = x, \geq 1$.

These products are obtained as clear, oily, yellow to deep red colored liquids. They can be dissolved without decomposition in moisture-free organic solvents such as, e.g., ethanol or N,N-dimethylformamide, in any ratio. They can be used directly in all applications without any intervening purification steps. Due to their high sulfur content and consequent large number of potential linking sites in the molecule, they are excellent silane binders or strengthening additives in silicate filled rubber mixtures It is surprising that according to the invention it is possible to produce oligo(4-(2-organo-organooxysilylalkyl)cyclohexane-1,2-diyl)-bis-oligosulfides without employing elevated pressures and without the use of sulfidization catalysts, and yet the method is without problems.

Other features of the invention will become apparent in the course of the following descriptions of exemplary embodiments which are given for illustration of the invention are not intended to be limiting thereof.

In a 250 ml three-neck flask with a stirrer, interior thermometer, reflux condenser, drying tube, and downstream condenser for gases which are evolved (cold trap employing dry ice and acetone), 100 g (0.367 mol) 4-(2-triethoxysilylethyl)-1-cyclohexene containing 0.1-5 g 4-(2-chlorodiethoxysilylethyl)-1-cyclohexene (molar ratio 965:1 to 19.3:1) and sulfur powder were reacted at 433°–443° K.

Figure 2:
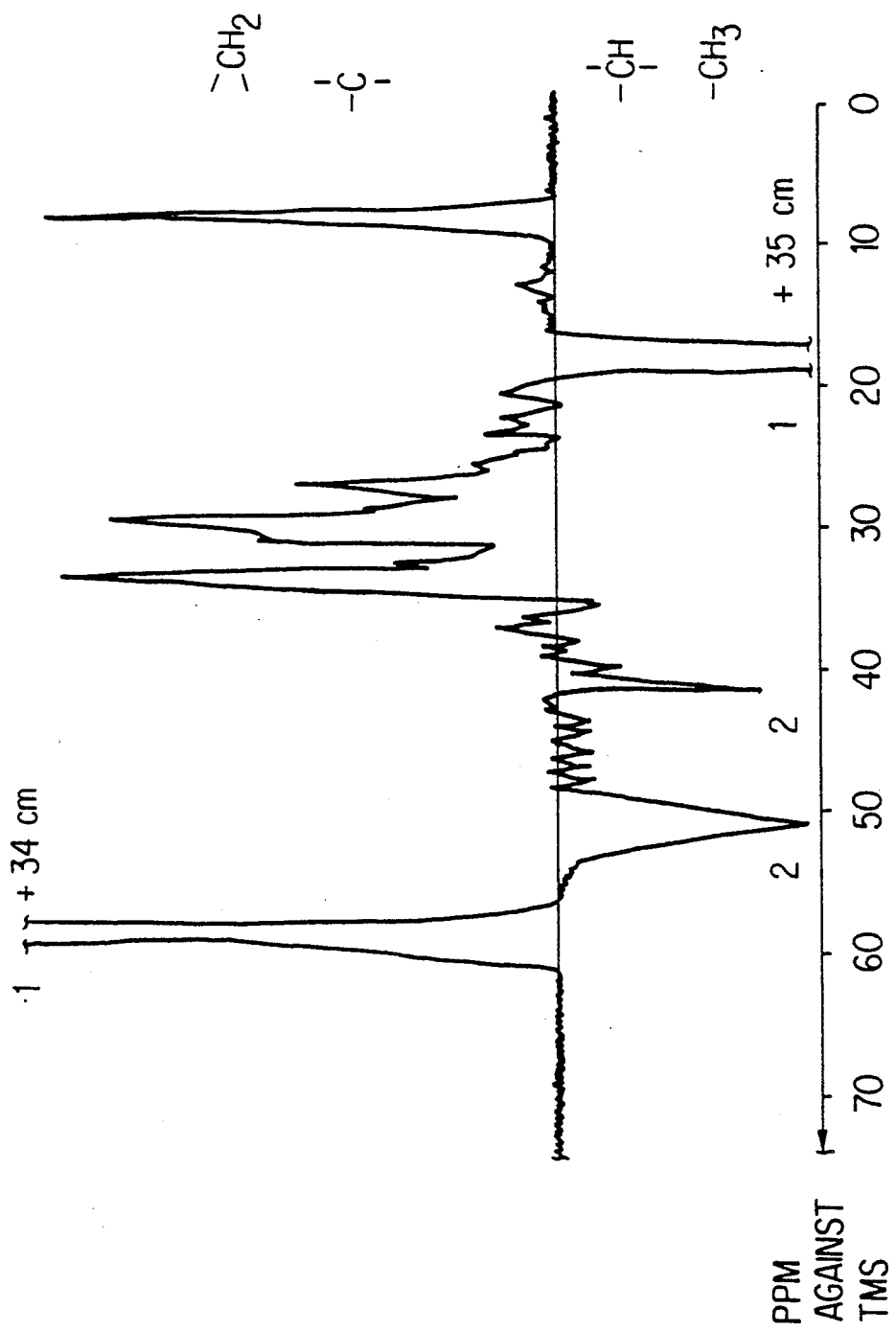
FIG. 2 sets out a $^{13}$C-NMR spectrum (Attached Proton Test) of the invention S-containing silanes according to Example 7.

After reaction for the given time, the sulfur had completely dissolved, with formation of the desired oligo(4-(2-triethoxysilylethyl)-cyclohexane-1,2-diyl)-bisoligosulfides. The reaction product was a clear, oily, colored liquid soluble in any ratio in moisture-free organic solvents such as ethanol, acetone, or N,N-dimethylformamide. If a small amount of sulfur precipitates out when the product is dissolved in moisture-free organic solvents, it may be removed by suction. Thestructure of the oligosulfides obtained was determined with the aid of $^{13}$C-NMR spectroscopy and high pressure liquid chromatography (FIGS. 1 and 2).

The starting substances, reaction times, and parameters of the reaction products for Examples 1–7 are given in Table 1.

The oligo(4-(2-triethoxysilylethyl)-cyclohexane-1,2-diyl)-bis-oligosulfides produced were tested for effectiveness as S-containing silane binders for silicate filled vulcanizable rubbers. The tests were carried out on a styrene-butadiene rubber mixture filled with silicic acid.

The composition of the SBR mixture used is given in Table 2. The dynamic, physical and mechanical parameters of the vulcanizates which parameters were obtained using the inventive products according to Examples 1, 4, and 7, with the null mixture for comparison, are given in Table 3.

TABLE 1

| Example Number | 1 | 2 | 3 | 4 | 5 | 6 | 7 |
| --- | --- | --- | --- | --- | --- | --- | --- |
| 4-(2-Triethoxysilylethyl)-1-cyclohexene-1 | | | | | | | |
| (grams) | 100 | 100 | 100 | 100 | 100 | 100 | 100 |
| (mol) | 0.367 | 0.367 | 0.367 | 0.367 | 0.367 | 0.367 | 0.367 |
| Content of 4-(2-chlorodiethoxysilylethyl)-1-cyclohexene | | | | | | | |
| (grams) | 0.1 | 0.1 | 0.5 | 1 | 3 | 5 | 0.15 |
| (mol) | 0.0004 | 0.0004 | 0.002 | 0.004 | 0.012 | 0.02 | 0.0006 |
| Sulfur | | | | | | | |
| (grams) | 23.5 | 35.3 | 35.3 | 35.3 | 35.3 | 35.3 | 47.1 |

TABLE 1-continued

| Example Number | 1 | 2 | 3 | 4 | 5 | 6 | 7 |
| --- | --- | --- | --- | --- | --- | --- | --- |
| (mol) | 0.734 | 1.1 | 1.1 | 1.1 | 1.1 | 1.1 | 1.468 |
| Reaction time (hour) | 2 | 3 | 3 | 3 | 3 | 3 | 3.5 |
| Yield (% of theoretical) | 99.6 | 92.9 | 98.1 | 99.5 | 99.6 | 99.6 | 95.4 |
| Analysis data (wt. %): C found | 50.17 | 49.10 | 46.47 | 45.84 | 45.79 | 45.80 | 43.99 |
| C calculated | 49.97 | 45.61 | 45.61 | 45.61 | 45.61 | 45.61 | 41.96 |
| H found | 8.42 | 8.24 | 7.80 | 7.70 | 7.69 | 7.71 | 7.38 |
| H calculated | 8.38 | 7.65 | 7.65 | 7.65 | 7.65 | 7.65 | 7.04 |
| S found | 18.70 | 20.44 | 24.70 | 25.70 | 25.01 | 25.80 | 28.72 |
| S calculated | 19.05 | 26.09 | 26.09 | 26.09 | 26.09 | 26.09 | 32.00 |
| Cl found | 0.01 | 0.01 | 0.05 | 0.11 | 0.34 | 0.61 | 0.02 |
| Cl calculated | 0.013 | 0.013 | 0.065 | 0.13 | 0.39 | 0.65 | 0.023 |
| Color of the product | yellow | yellowish orange | yellowish orange | yellowish orange | yellowish orange | yellowish orange | orangish red |

TABLE 2

Composition of the silicic-acid-filled SBR test mixture

| Components (parts by wt. per 100 parts by wt. of the rubber) | Null Mixture | Test Mixtures 1, 2 and 3 |
| --- | --- | --- |
| Buna SB 152H (a styrene-butadiene rubber) | 100 | 100 |
| Filler K 605 (silicic acid with pH 7.6–8.4) | 40 | 40 |
| Softener SE (paraffin oil) | 10 | 10 |
| Zinc white WS (ZnO) | 5 | 5 |
| Stearic acid | 2 | 2 |
| Anti-aging agent MB (2-methylbenzimidazole) | 1 | 1 |
| Chalk (inactive fiber) | 5 | 2 |
| Sulfenaz CB 30 (N-cyclohexyl-2-benzothiazyl-sulfenamide) | 1.5 | 1.5 |
| Wobazid Thiuram OS (tetramethylthiuram disulfide ultra-accelerator) | 0.3 | 0.3 |
| Sulfur dispersion T | 2.5 | 2.5 |
| Test substance (inventive silane corresponding to Example 1, 4 or 7) | — | 3 |
| Sum | 167.3 | 167.3 |

TABLE 3

Dynamic, physical and chemical parameters of the vulcanization produced

| Parameter of the rubber | Null mixture | Test mixture with the silane according to Example 1 | Example 4 | Example 7 |
| --- | --- | --- | --- | --- |
| $M_L$ viscosity (rheometer units) | 14.8 | 13.3 | 13.2 | 13.0 |
| $t_2$ Scorch time (torque at 90% of the vulcanization time) (min:sec) | 9:22 | 8:09 | 7:23 | 6:33 |
| $t_{90}$ Scorch time (torque at 90% vulcanization) (min:sec) | 32:05 | 18:08 | 15:42 | 17:24 |
| 90% of the maximum torque of the fully vulcanized mixture (rheometer units) | 70.0 | 71.6 | 74.5 | 74.6 |
| Modulus 100 (resistance force at 100% elongation) (mPa) | 2.09 | 2.75 | 2.81 | 3.72 |
| Modulus 200, after aging 7 da at 70° C. | 2.64 | 3.94 | 4.60 | 5.17 |
| Modulus 200 | 3.70 | 5.60 | 5.68 | 7.04 |
| Modulus 200, after aging 7 da at 70° C. | 4.44 | 8.09 | 8.56 | 9.04 |
| Modulus 300 | 5.19 | 8.31 | 8.35 | 9.71 |
| Modulus 300, after aging 7 da at 70° C. | 6.77 | 11.05 | 11.62 | — |
| Strength at elongation to failure (mPa) | 11.21 | 11.47 | 12.07 | 11.09 |
| Strength, after aging 7 da at 70° C. | 10.60 | 10.62 | 11.56 | — |
| Tensile strength (measure for strength after aging) (%) | 5.4 | 9.1 | 10.7 | 12.1 |
| Elongation at failure (%) | 490 | 392 | 341 | 298 |
| Elongation, at failure after aging 7 da at 70° C. | 407 | 243 | 258 | 196 |
| Elongation of control (%) | 16 | 9 | 9 | 9 |
| Hardness (Shore A units) | 52 | 54 | 56 | 56 |
| Resilient elasticity (%) | 36 | 30 | 39 | 40 |
| Residual deformation under compression (%) | 62.5 | 51.9 | 53.5 | 49.7 |

The inventively produced oligo(4-(2-triethoxysilylethyl)cyclohexane-1,2-diyl)-bis-oligosulfides in the silicic-acid-filled SBR mixture caused reduction of the Mooney viscosity $M_L$ and reduction of the pre-vulcanization and vulcanization times ($t_2$ and $t_{90}$) without going below the safety limit of 5 minutes for industrial rubber practice.

Further, nearly all the physical and mechanical properties of the vulcanizates obtained are superior to those of the null mixture. This means improved performance of the resulting rubber products in all potential applications.

Obviously, numerous modifications and variations of the present invention are possible in light of the above teachings. It is the refore to be understood that within the scope of the appended claims, the invention may be practiced otherwise than as specifically described herein.

What is claimed as new and desired to be secured by Letters Patent of the United States:

1. A method of manufacturing oligo(4-(2-organooxysilylalkyl)cyclohexane-1,2-diyl)bis-oligosulfides from products of industrial-scalesynthe sis of 4-(2-organoorganooxysilylalkyl)-1-cyclohexene, without the use of catalysts and at ambient pressure; comprising reacting an organosilane of formula I

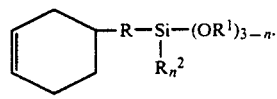

and an organochlorosilane of formula II

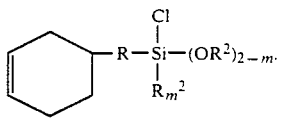

wherein R and R² each independently represent an C₁₋₆ alkyl group;
R¹ represents an alkyl, cycloalkyl, or aryl group;
n = 1 to 3; and
m = 1 or 2;
wherein the molar ratio of I to II is in the range of from 1000:1 to 10:1,
directly with sulfur or a mixture of hydrogen sulfide and sulfur, in a molar ratio of R: sulfur (and/or hydrogen sulfide) of 1:1 to 1:5, at a temperature > 150° C. and ambient pressure; and wherein said reaction is conducted in the absence of a sulfidization catalyst.

2. The method according to claim 1; characterized in that the reaction is carried out in the temperature range of 150°–200° C.

3. The method according to claims 1 or 2; characterized in that the molar ratio of I to II is in the range 1000:1 to 100:1.

4. The method according to claim 1; wherein when a mixture of hydrogen sulfide and sulfur is added, the weight fraction of the sulfur (based on the amount of the silane employed) is in the range 0.01 to 0.1.

5. The method of claim 1 wherein said ambient pressure is in the range of from 0.8–1.2 atmospheres 6. The method of claim 1 wherein said ambient pressure is in the range of from 0.95–1.05 atmospheres.

* * * * *

UNITED STATES PATENT AND TRADEMARK OFFICE
CERTIFICATE OF CORRECTION

PATENT NO. : 5,110,969

DATED : May 5, 1992

INVENTOR(S) : Uwe DITTRICH et al

It is certified that error appears in the above-identified patent and that said Letters Patent is hereby corrected as shown below:

Column 2, Formula I, change "$R_n^2$" to --$R^2_n$--.

Formula II, change "$R_m^2$" to --$R^2_m$--.

Column 3, Formula I, change "$R_n^2$" to --$R^2_m$--.

Formula II, change "$R_m^2$" to --$R^2_m$--.

Formula III, change "$R_n^2$" to --$R^2_n$--.

Column 6, Formula I, change "$R_n^2$" to --$R^2_n$--.

Column 7, Formula II, change "$R_m^2$" to --$R^2_m$--.

Front Page, Formula I, change "$R_n^2$" to --$R^2_n$--.

Front Page, Formula II, change "$R_m^2$" to --$R^2_m$--.

Column 4, line 32, change "bisoligo" to --bis-oligo--.

Column 4, line 38, change "Thestructure" to --The structure--.

Column 6, line 25, change "the refore" to --therefore--.

UNITED STATES PATENT AND TRADEMARK OFFICE
CERTIFICATE OF CORRECTION

PATENT NO. : 5,110,969

DATED : May 5, 1992

INVENTOR(S) : Uwe Dittrich, et al

It is certified that error appears in the above-identified patent and that said Letters Patent is hereby corrected as shown below:

Column 6, line 33, change "scalesynthe sis" to --scale synthesis--.

Signed and Sealed this

Tenth Day of August, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,110,969
DATED : MAY 5, 1992
INVENTOR(S) : UWE DITTRICH ET AL

It is certified that error appears in the above-indentified patent and that said Letters Patent is hereby corrected as shown below:

Column 2, Formula I, change "$R_n^2$" to --$R^2_n$--.

Formula II, change "$R_m^2$" to --$R^2_m$--.

Column 3, Formula I, change "$R_n^2$" to --$R^2_n$--.

Formula II, change "$R_m^2$" to --$R^2_m$--.

Formula III, change "$R_n^2$" to --$R^2_n$--.

Column 6, Formula I, change "$R_n^2$" to --$R^2_n$--.

Column 7, Formula II, change "$R_m^2$" to --$R^2_m$--.

Front Page, Formula I, change "$R_n^2$" to --$R^2_n$--.

Front Page, Formula II, change "$R_m^2$" to --$R^2_m$--.

Column 4, line 32, change "bisoligo" to --bis-oligo--.

Column 4, line 38, change "Thestructure" to --The structure--.

Column 6, line 25, change "the refore" to --therefore--.

UNITED STATES PATENT AND TRADEMARK OFFICE
CERTIFICATE OF CORRECTION

PATENT NO. : 5,110,969
DATED : MAY 5, 1992
INVENTOR(S) : UWE DITTRICH ET AL

It is certified that error appears in the above-indentified patent and that said Letters Patent is hereby corrected as shown below:

Column 6, line 33, change "scalesynthe sis" to

--scale synthesis--.

This certificate supersedes Certificate of Correction issued August 10, 1993.

Signed and Sealed this

Twelfth Day of October, 1993

*Attest:*

BRUCE LEHMAN

*Attesting Officer*   *Commissioner of Patents and Trademarks*